United States Patent [19]

Dorawala et al.

[11] 4,139,491

[45] Feb. 13, 1979

[54] NOVEL METHOD FOR PREPARING A HIGH PURITY ALUMINA

[75] Inventors: Tansukhlal G. Dorawala; Edwin R. Kerr, both of Wappingers Falls; Robert G. Kochis; Leon F. Koniz, both of Poughkeepsie, all of N.Y.

[73] Assignee: Texaco Inc., New York, N.Y.

[21] Appl. No.: 888,591

[22] Filed: Mar. 20, 1978

Related U.S. Application Data

[63] Continuation of Ser. No. 665,834, Mar. 11, 1976, abandoned.

[51] Int. Cl.$^2$ ............... B01J 27/02; B01J 31/02; B01J 27/24; B01J 21/00
[52] U.S. Cl. ............... 252/440; 252/430; 252/436; 252/438; 252/463

[58] Field of Search ............... 252/440, 463, 436, 438, 252/430

[56] References Cited

U.S. PATENT DOCUMENTS 4,019,978  4/1977  Miller et al. ............... 252/463 X

*Primary Examiner*—Delbert E. Gantz
*Assistant Examiner*—William G. Wright
*Attorney, Agent, or Firm*—Thomas H. Whaley; Carl G. Ries; Carl G. Seutter

[57] ABSTRACT

A novel active alumina which has been treated with sulfate ion, is found to be particularly characterized by increased performance when used as a support for catalyst which may be used in hydrocarbon conversion processes such as steam dealkylation.

26 Claims, No Drawings

NOVEL METHOD FOR PREPARING A HIGH PURITY ALUMINA

This is a continuation of application Ser. No. 665,834, filed Mar. 11, 1976 now abandoned.

FIELD OF THE INVENTION

This invention relates to a novel alumina and to a method of preparing the novel product. More particularly it relates to the use of a novel catalyst system, including a novel alumina catalyst support, which permits attainment of desired levels of conversion, yield, and selectivity in hydrocarbon conversion processes, typically steam-dealkylation.

BACKGROUND OF THE INVENTION

As is well known to those skilled in the art, various catalyst are used in processing. Many of these catalysts are characterized by the presence of catalytically active components on a support. Attempts are constantly being made to improve the properties of the support and to thus permit attainment of a catalyst composition, containing support preferably plus other ingredients, which is characterized by desirable properties including, for example, conversion, yield, selectivity, etc.

It is an object of this invention to provide a novel alumina, and a process for making this product. Other objects will be apparent to those skilled in the art.

STATEMENT OF THE INVENTION

In accordance with certain of its aspects, this invention is directed to a method of preparing a treated high purity alumina characterized by improved activity and containing a catalytic amount of sulfate anion together with at least one catalytically acceptable cation which comprises adding to a charge high purity alumina a catalytic amount of a sulfate anion together with a catalytically acceptable cation;

maintaining said charge alumina in contact with said catalytic amount of sulfate ion whereby said sulfate ion is distributed over the outside of said charge alumina and throughout substantially the entire body of said alumina thereby forming desired product treated alumina containing a catalytic amount of sulfate anion together with at least one catalytically acceptable cation; and recovering said desired product treated alumina containing a catalytic amount of sulfate anions together with at least one catalytically acceptable cation.

DESCRIPTION OF THE INVENTION

The high purity aluminas which may be used as charge in practice of the process of this invention are typically substantially pure alumina i.e. $Al_2O_3$. These aluminas are commonly characterized by the fact that they contain little or no measurable content of metal impurities the amounts present usually being measured in parts per million and commonly are found to be less than 100 ppm. In particular, these aluminas may be essentially free of sulfate ion and they may contain less than eg 0.15% sulfate i.e. less than 1500 ppm sulfate, and frequently (depending on the particular source or mode of preparation) less than that.

Typical of these high purity sulfate-free aluminas which may be available may be:

(i) alumina derived from chemically pure aluminum hydroxide which is obtained as by dehydration of the precipitate obtained by reaction of a soluble salt of aluminum (such as aluminum acetate) and a base (such as ammonium hydroxide);

(ii) alumina derived from chemically pure aluminum which is obtained by dissolving the aluminum in a solvent (eg caustic soda to form sodium aluminate) from which aluminum hydroxide is precipitated (eg by addition of acid), the hydroxide being dehydrated to alumina;

(iii) alumina derived by combustion of aluminum metal;

(iv) alumina found naturally occurring in pure state as a mineral;

(v) alumina recovered as by-product from chemical reactions wherein, because of the nature of the reaction or the normal recovery technique, the alumina is recovered in substantially pure form; etc.

Typical of such pure aluminas is the Capatal-S type of alumina derived as a by-product from the preparation of alcohols by a process which uses aluminum alcoholates. U.S. Pat. No. 2,892,858, for example, discloses a Zeigler synthesis of higher alcohols and the formation of such a by-product alumina.

The Capatal-S type alumina (which is typical of the aluminas which may be used in practice of this invention) may typically contain no measurable content of alkali metal when measured as sodium by standard analytical techniques. The principal impurity normally is titanium dioxide $TiO_2$ in amount (as $TiO_2$) of 150–700 ppm, typically 500–700 ppm, say 600 ppm. Other impurities typically include: $SiO_2$ silicon dioxide in amount (as $SiO_2$) of 80–120 ppm, say 100 ppm; iron oxides in amount (as $Fe_2O_3$) of 27–61 ppm, say 40 ppm, alkaline earth metals in amount (as MgO) of 14–70 ppm, say 50 ppm; and alkali metals in amount (as $Na_2O$) too low to determine by the usual analytical techniques. The titanium, silicon, iron, and alkaline earth metals are present as oxides (either as such or as in complexes); and for convenience the concentration is reported as pure metal. The alumina may be substantially free of other impurities.

This high-purity alumina, like the other high purity aluminas which may be used in practice of the process of this invention, is particularly characterized by its substantial freedom from sulfate or similar anions; and sulfate, if present at all, is typically present in amounts less than about 1500 ppm, say 300–900 ppm or even less.

Although the high purity of the Capatal S-type alumina, and the other aluminas obtained therefrom including Capatal S-type gamma alumina, would seem to suggest that they may be particularly useful in applications which would apparently be benefitted by this low level of impurities, in practice this is not found to be so. If pure gamma alumina derived from a Capatal S alumina for example be used eg in a catalyst for the steam dealkylation of hydrocarbons such as toluene, it is found that, undesirably, the benzene yield, benzene selectivity, etc. are substantially less than is desired — and specifically much less than may be attained by the process of this invention. The yield may be a third less and the selectivity may be a third less.

These observations are also found in the case of other high-purity aluminas which typically contain less than about 1500 ppm of sulfate (i.e. 0.15%) including for example Capatal-S-type alpha alumina monohydrate, alpha alumina trihydrate, etc, which may be readily converted to gamma alumina, a preferred support for catalyst in many reactions.

It has unexpectedly been found, if one uses a high purity alumina as a basis for preparing a catalyst support, that the results are found to be unsatisfactory. Alternatively expressed, it has been found that if one uses prior art high quality alumina, the results are found to be erratic-to-unsatisfactory.

It has been unexpectedly found that the reason these high-purity aluminas do not function effectively in many catalytic processes is because they are "too pure" i.e. they contain sulfate ion in amount less than about 1500 ppm; and it is now found that presence of a catalytic amount of sulfate is usually necessary (and at the very least helpful) in attaining maximum activity of catalysts prepared from so-called pure aluminas.

In practice of this invention, there may be added to the alumina a catalytic amount of sulfate anion together with at least one catalytically acceptable cation. Although the sulfate anion may be added for example to an alpha alumina monohydrate Capatal S or to any of the aluminas to which it may be converted during processing, it is preferred to add the sulfate ion to the Capatal S-derived (otherwise pure except for its content of titanium dioxide) gamma alumina.

A catalytic amount of sulfate ion is commonly about 0.3–0.9% of the support more preferably 0.45–0.6%, say about 0.45% of the support. Since a typical catalyst contain other components (eg metals, oxides, etc) this may correspond to about 0.2–0.6%, more preferably 0.27–0.41%, say about 0.3% of the total catalyst containing support plus metals etc. Analytically this value is sometimes reported as "wt % sulfur (as sulfate)"; this is an equivalent way of defining the catalytic amount of sulfate ion.

Amounts of sulfate ion in excess of the noted maximum tend to give decreased yields, while amounts below the noted minimum, tend to give both decreased yield and selectivity.

The sulfate ion is present together with a catalytically acceptable cation. Catalytically acceptable cations may include any cations which are found in sulfate compounds and which do not produce a detrimental or undesirable effect on the catalyst system. Catalytically acceptable cations may include those which appear to be inert, or those which moderate the catalytic activity, or those which possess desirable independent catalytic activity, or those which augment or promote the desired catalytic activity.

It will be apparent to those skilled in the art that the nature of the catalytically acceptable cations will be dependent on the ultimate catalytic process in which the catalyst is to be used. Common catalytically acceptable cations include (i) hydrogen (as in sulfuric acid); (ii) organic cations which are volatilizable or decomposable (as in alkyl sulfates such as methyl sulfate, ethyl sulfate, etc.); (iii) cations which are to be included in the final catalyst composition — e.g. if the final composition is to include, e.g. nickel, then the sulfate may be added as nickel sulfate subject to the maximum quantity of nickel which it may be desirable to have present in the catalytic composition.

The preferred cations are hydrogen or aluminum; and preferred compounds by which sulfate may be added include sulfuric acid, aluminum sulfate, and ammonium sulfate.

It may be possible within the scope of this invention to use sulfate precursors such as (a) bisulfates (typified by potassium bisulfate); or (b) organic sulfonic acids typified by benzene sulfonic acid, toluene sulfonic acids, etc.; or (c) sulfites (including potassium sulfite) or sulfur dioxide; or (d) bisulfites (including potassium thiosulfate); or (f) persulfates (including persulfuric acid or fuming sulfuric acid) which under the conditions of oxidation prevailing may impart the desired properties to the alumina.

It is possible for example to introduce the desired sulfate ion (i) into an alpha alumina trihydrate before, during, or after its conversion to the alpha alumina monohydrate; (ii) into an alpha alumina monohydrate prior to, during, or after its conversion to gamma alumina; (iii) into a gamma alumina prior to, during or after further treatment; etc.

Specifically it may be possible to introduce sulfate ion (i) after the final catalyst composition including alumina plus metals is formulated; (ii) prior to, concurrently with, or immediately after addition of any one of the catalyst component metals; (iii) before or after any of the drying or calcination steps.

It is, however, preferred that the catalytic amount of sulfate ion and catalytically acceptable cation be added to the calcined gamma alumina prior to addition thereto of the other components of the finished catalyst composition. Preferably the so-obtained gamma alumina contains a catalytic amount of sulfate ion distributed over the outside of the alumina and throughout substantially the entire body of the alumina.

Preferred of these sulfate ion compositions are sulfuric acid and ammonium sulfate and aluminum sulfate.

It will be apparent that the preferred catalytically acceptable cation be one having a soluble sulfate. Metals such as barium, calcium, and strontium, when present as their sulfates, tend to give somewhat lower conversion with lower yield of desired product and they also tend to give increased concentration of undesired by-products in various hydrocarbon conversion reactions such as steam demethylation.

The high purity alumina which may be used to prepare the catalyst of this invention is typically an alumina in the form of an extrudate of 1.5 mm diameter and 10 mm length which may be steam sintered at 900° F.–1400°0 F., say 1100° F. for 5–25 hours, say 12 hours. During sintering, air may be passed through the catalyst bed in amount of 5–20, say 8 cubic feet per hour per 1000 cc of catalyst together with steam in amount of 50–100, say 64 grams per hour per 1000 cc of catalyst. The steamed alumina is then calcined for 1–5 hours, say 2 hours at 900° F.–1200° F., say 1000° F. This support is then cooled to 32° F.–80° F., say about 72° F. and thereafter impregnated with desired sulfate ions.

In practice of the preferred embodiment, 100 parts of e.g. gamma alumina may be immersed in 10–300 parts, say 73 parts of aqueous solution containing 0.15–10.0 parts, say 0.47 parts of sulfate ion. This may correspond, for example, to 0.153–10.2 parts, say 0.48 parts of sulfuric acid; or to 0.178–11.9 parts, say 0.98 parts of aluminum sulfate $Al_2(SO_4)_3$; etc.

The gamma alumina is allowed to remain in contact with the aqueous solution at 50° F.–160°0 F., say 78° F. for 0.5–24 hours, say 1 hour. If desired, impregnation may be effected by use of a portion of the aqueous solution which is allowed to contact the alumina for 0.25–24 hours, say 1 hour. This portion of solution may then be poured off and replaced by a second portion which is allowed to contact the alumina for 0.25–24 hours, say 1 hour.

The alumina, now bearing the catalytic amount of sulfate ion distributed over the outside of the alumina and throughout substantially the entire body of alumina is then dried at 200° F.–500° F., say 300° F. for 0.25–24 hours, say 1 hour. The so-dried alumina is preferably then calcined at 700° F.–1400° F., say 1000° L. F. for 0.25–24 hours, say 2 hours.

The alumina so prepared may be found to contain 0.3 w%–0.9 w%, say 0.45 w% of sulfate ion.

The so-prepared alumina may be a novel gamma alumina containg a catalytic amount (typically 0.3 w%–0.9 w%, preferably 0.45 w%–0.6 w%, say 0.45 w%) of sulfate anion distributed over the outside of said gamma alumina and throughout substantially the entire body of said gamma alumina — together with at least one catalytically acceptable cation.

It will be apparent to those skilled in the art that when the sulfate is added in the form of sulfuric acid, the catalytically acceptable cation may be considered to be hydrogen. In this instance, it is probable that the sulfuric acid may react with a portion of the alumina to form aluminum sulfate and water, which latter may be expelled during calcination; and thus the catalytically acceptable cation may alternatively be considered to be aluminum. Similar considerations may prevail when the sulfate is added as ammonium sulfate, methyl sulfate, etc., wherein the ammonium or methyl, etc. cations may be volatilized etc. under conditions of calcining to leave aluminum as the net catalytically acceptable cation.

It is particularly unexpected to fine that high purity prior art aluminas typified by Catapal S-types or by others (prepared e.g. by precipitation of high purity aluminum hydroxide from sulfate-free solutions) may possess undesirable properties because they do not contain sulfate ion; it is particularly unexpected to find that prior art sulfate-free aluminas may be modified to enhance their catalytic properties by the addition thereto of sulfate ion.

Although catalyst compositions prepared by the process of this invention may be useful for hydrogenation, hydrocracking, transalkylation, disproportionation, or other reactions (depending upon the catalytic metals or components subsequently added and the conditions of reaction), it is found that particularly desirable results may be achieved when the so-prepared alumina is used in steam dealkylation. Accordingly, the preparation of a typical catalyst for steam demethylation of toluene will be used as the typical preferred catalyst for description.

The catalyst composition which may be employed in practice of the steam dealkylation process of this invention may comprise a catalyst support as described supra and, disstributed thereon, and therein oxides of (i) a Group VIII metal, (ii) preferably a Group VIB metal, and (iii) preferably a Group IA metal.

The Group VIII metal may include iron Fe, cobalt Co, nickel Ni, ruthenium Ru, rhodium Rh, palladium Pd, osmium Os, iridium Ir, and platinum Pt. Preferably the Group VIII metal may be nickel or cobalt; and in the most preferred embodiment, it is nickel.

The Group VIB metal may be chromium Cr, molybdenum Mo, or tungsten W; and in the preferred embodiment, it is chromium Cr.

The Group IA metal, an alkali metal, may be lithium Li, sodium Na, potassium K, rubidium Rb or cesium Cs. In the preferred embodiment, it is potassium K.

In typical practice of the process of this invention, the catalyst composition may contain the following components in the indicated parts by weight (expressed as oxide).

In this table and in the others which follow, the metals are expressed as parts by weight of oxide. Thus, Group VIII - 15 parts means that the composition contains Group VIII metal in amount sufficient to make 15 parts of the corresponding oxide eg NiO or Fe$_2$O$_3$. The support is expressed as parts by weight of eg alumina. The sulfate anion is expressed as parts by weight of sulfate; and it will be apparent that the corresponding cation (which is not included in the stated parts by weight of the sulfate) may be one of metals of Groups VIII, VI B, or I A or any other compatible cation such as H$^+$, NH$_4$$^+$, etc.

TABLE

| Component | Broad | Preferred | Typical |
|---|---|---|---|
| Group VIII | 0.5 – 40 | 5 – 20 | 15 |
| Group VIB | 0 – 40 | 10 – 38 | 15 |
| Group IA | 0 – 5 | 1 – 4 | 2 |
| Support | 15 – 99.5 | 46 – 84 | 68 |
| SO$_4$= | 0.2 – 0.6 | 0.27 – 0.41 | 0.3 |

The preferred catalyst may be that containing nickel-chromium-potassium-aluminum sulfate; and the catalyst composition may contain the following (or expressed as noted supra):

TABLE

| Component | Broad | Preferred | Typical |
|---|---|---|---|
| Ni | 6 – 40 | 5 – 20 | 15 |
| Cr | 0 – 40 | 10 – 38 | 15 |
| K | 0 – 5 | 1 – 4 | 2 |
| Al$_2$O$_3$ | 15 – 95 | 46 – 84 | 68 |
| SO$_4$ | 0.20 – 0.6 | 0.27 – 0.41 | 0.3 |

In terms of *molar* proportions, the catalyst may be represented by the formula

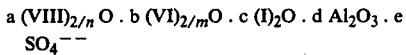

a (VIII)$_{2/n}$O . b (VI)$_{2/m}$O . c (I)$_2$O . d Al$_2$O$_3$ . e SO$_4$$^{--}$ wherein (VIII) represents a metal of Group VIII of the Periodic Table having a valence n, (VI) represents a metal or Group VIB of the Periodic Table having a valence m, (I) represents a metal of Group IA of the Periodic Table. a may be 0.002–0.75, preferably 0.002–0.38, say 0.2; b may be 0–0.78, preferably 0.13–0.75; say 0.29 c may be 0–0.05, preferably 0.01–0.04, say 0.02; d is 0.15–0.995, preferably 0.46–0.84, say 0.68, and e is 0.002–0.006, preferably 0.0027–0.004, say 0.003.

In a preferred embodiment, the catalyst may be represented by the formula

a NiO . b Cr$_{2/3}$O . c K$_2$O . d Al$_2$O$_3$ . e SO$_4$$^{--}$ wherein a is 0.08–0.54, preferably 0.08–0.27, say 0.2; b is 0–0.78 preferably 0.21–0.75, say 0.29; and c is 0–0.05, preferably 0.01–0.04 say 0.02; d is 0.15–0.95, preferably 0.46–0.87 say 0.68; and e is 0.002–0.006 preferably 0.0027–0.004, say 0.003.

In practice of one aspect of this invention, the catalyst may be prepared by immersing the catalyst support containing sulfate ions in a solution containing the metal ions.

The support (242 parts), preferably containing sulfate ions is cooled to 32° F.–80° F., say about 72° F. and wetted with 200–2525 parts, say 250 parts of solution prepared by dissolving soluble decomposable salts of metals of Group VI B and Group I A in aqueous solution; 0-1000 parts, preferably 500-1000 parts, say 792 parts of salt of Group VI B metal, typically chromium nitrate nonahydrate Cr $(NO_3)_3.9H_2O$ and 0-25 parts, preferably 10-20 parts, say 17.2 parts of salt of Group I A metal, typically potassium nitrate are dissolved in 50-500 parts, say 80 parts of water to yield total solution in amount of 20-2525 parts, say 890 parts. (Although nitrates of the metals are preferably employed, acetates, formates, citrates, or other soluble decomposable salts may be used).

The support preferably containing sulfate ions, is permitted to stand for 0.5-30 hours, say 10 hours and the solution (0-1000 parts, typically 460 parts) is decanted. The impregnated support is dried at 212° F.-400° F., say 300° F., then heated to decomposition temperature of typically 650° F.-1000° F., say 700° F., and calcined for 1-10 hours, say 2 hours at 700°-1400° F., say 1000° F. This procedure is preferably repeated 2-4, preferably 2 times more until all the metal salt solution is absorbed by the support. The final precatalyst so prepared in amount of 242-1500 parts, say 383 parts may be characterized by the formula $$b (VI)_{2/m} O \cdot c (I)_2 O \cdot d\, Al_2O_3 \cdot e\, SO_4^{--}$$

wherein (VI) represents a metal of Group VI B of the Periodic Table having a valence m, (I) represents a metal of Group I A of the Periodic Table, b is 0-0.78, preferably 0.13-0.75 say 0.74, c is 0-0.05, preferably 0.01-0.04, say 0.02, d is 0.15-0.95, preferably 0.38-0.84, say 0.59 and e is 0.002-0.006, preferably 0.0027-0.004, say 0.003.

In the preferred embodiment, the composition of pre-catalyst may be $$b\, Cr_2O_3 \cdot c\, K_2O \cdot d\, Al_2O_3 \cdot e\, SO_4^{--}$$

wherein b is 0.25 c is 0.02, d is 0.59, and e is 0.003 242-1500 parts, say 383 parts of precatalyst may be cooled to 32° F.-80° F., say 72° F. and impregnated with a decomposable salt of a Group VIII metal. Preferably the solution may contain 50-700 parts, say 250 parts of $Ni(NO_3)_2.6H_2O$ in 50-700 parts, say 263 parts of water. After 0.5-30 hours, say 10 hours, the excess non-absorbed solution is decanted and the solids dried for 2-4 hours, say 2 hours at 212° F.-400° F., say 300° F. The dried solid is reimpregnated with the remaining salt solution for 0.5-30 hours, say 10 hours, and dried again for 2-4 hours, say 2 hours at 212° F.-400° F., say 300° F. Further treatment includes heating for 0.5-30 hours, say 1 hour at 650° F.-1000° F., say 700° F. in flowing air to decompose the decomposable salts, typically nitrates, and calcining for 1-10 hours, say 2 hours at 600° F.-900° F., say 700° F. to yield 260-1850 parts, say 462 parts having a density of 0.7-1.5, say 1.11.

A product catalyst so prepared may be characterized by the formula:

$$a(VIII)_{2/n}O \cdot b(VI)_{2/m}O \cdot c(I)_2O \cdot d\, Al_2O_3 \cdot e\, SO_4^{--}$$

wherein all the symbols are as noted supra except that a is 0.002-0.75, preferably 0.002-0.38, say 0.2, (VIII) represents a metal of valence n of Group VIII of the Periodic Table, preferably nickel, and $Al_2O_3$ represents the alumina support, preferably gamma alumina.

Preferred catalyst compositions may have the formulae:

$$0.25 NiO \cdot 0.27 Cr_{2/3}O \cdot 0.02 K_2O \cdot 0.64 Al_2O_3 \cdot 0.003 SO_4^{--}$$

$$0.18 NiO \cdot 0.54 Cr_{2/3}O \cdot 0.02 K_2O \cdot 0.51 Al_2O_3 \cdot 0.004 SO_4^{--}$$

$$0.2 CoO \cdot 0.2 Cr_{2/3}O \cdot 0.02 Na_2O \cdot 0.40 Al_2O_3 \cdot 0.0027 SO_4^{--}$$

Expressed on a weight basis, the catalyst may have the composition set forth in the following table:

TABLE

| Component | Broad | Preferred | Typical |
|---|---|---|---|
| $(VIII)_{2/n}O$ | 0.5 –40 | 5 –20 | 17.7 |
| $(VI)_{2/m}$ | 0 –40 | 10 –30 | 13.2 |
| $(I)_2$ | 0 –5 | 1 –4 | 1.9 |
| $(Al_2O_3)$ | 15 –99.5 | 46 –84 | 61.6 |
| $SO_4^=$ | 0.2 –0.6 | 0.27 –0.41 | 0.3 |

A preferred composition may contain 17.7% NiO, 13.2% $Cr_{2/3}O$, 1.9% $K_2O$, 61.6% $Al_2O_3$, and 0.30% $SO_4^{--}$ Another preferred composition may contain 19.9% NiO, 15.2 $Cr_{2/3}O$, 1.95% $K_2O$, 56.9% gamma alumina, and 0.41% $SO_4^{--}$.

The catalyst composition of this invention may be prepared by impregnating the alumina support with solutions of metal of Groups VIII, VI B, and/or I A. Typically, for example, it may be found that the catalyst may be prepared by:

(a) impregnating the support with a single solution containing all the metals, drying, and calcining;

(b) impregnating the support sequentially with the several solutions each containing one or more of the metals and thereafter drying and calcining;

(c) impregnating the support with one or more solutions containing less than all of the metals (i.e. species or amount), drying and/or calcining, thereafter impregnating the support with the remaining metals, and drying and/or calcining; etc.

It is unexpectedly found however that substantially superior results are achieved (in terms of conversion, yield, and/or selectivity) if the Group VI B and I A metals are dried and calcined on the catalyst support prior to the impregnation thereof with the Group VIII metal.

In the preferred embodiment, the catalyst support may thus be prepared by impregnating the support, typically alumina, with one solution containing soluble decomposable salts of the Group VI B and Group I A metals, typically chromium and potassium, drying and calcining, thereafter impregnating the so-obtained precatalyst with a solution of a soluble decomposable salt of the Group VIII metal, typically nickel, and drying and calcining.

The sulfate content of the alumina, or the alumina-derived catalyst, may be added to the high purity (eg sulfate-free aluminas) ab initio or at any desired stage during processing. For example the sulfate content could be added at any stage in the interconversion of alpha monohydrate, alpha trihydrate, or beta trihydrate to gamma alumina. It may be added during further treating i.e. before or during or as an integral step in addition of other components — eg as by addition of nickel sulfate etc.

In the preferred embodiment, the catalyst composition may be in the form of pellets, cylinders, or randomly shaped particles; a typical catalyst composition may be in the form of cylinders, of diameter equal to height, of 10 mm.

It is a feature of the preferred catalyst of this invention that it be activated prior to use (e.g. in steam dealkylation). Preferably activation may be carried out in the process which comprises (a) maintaining the unactivated catalyst in a hydrogen atmosphere at 750° F.-1400° F. for 0-30 hours thereby forming a hydrogen-treated catalyst;

(b) maintaining the hydrogen-treated catalyst in steam-hydrogen atmosphere at 750° F.-1400° F. for 2-10 hours thereby forming a steamed hydrogen treated catalyst; and (c) cooling the steamed hydrogen-treated catalyst to 650° F.-900° F. in a steam or steam-hydrogen atmosphere thereby forming an activated catalyst.

Activation of the steam dealkylation catalyst of this invention may preferably be carried out after the catalyst is in place in the reaction vessel. The vessel may be filled with catalyst composition to a bed bulk density of 50-80 pcf, say 70 pcf. In the first portion of the activation operation, the catalyst composition is heated to 750° F.-1400° F., preferably 900° F.-1100° F., say 1100° F. in the presence of inert gas containing at least about 30 mole % hydrogen. The inert gas will preferably be substantially free of active components which are capable of reacting with any of the materials in the system. It is particularly desirable that the gas be free of oxidizing components including oxygen.

The gas may contain helium or more preferably light paraffins such as methane, ethane, propane, etc. Hydrogen may be present typically in amount of 30 mole %-100 mole %, preferably 80 mole %-100 mole %, say 100 mole % — i.e. the preferred embodiment may be that in which the gas consists essentially of hydrogen.

Preferably the catalyst composition may be maintained for 10-30 hours, typically 14-16 hours, say 15 hours in a stream of flowing hydrogen typically flowing at a space velocity VHSV greater than about 3, more preferably greater than 100, say 100-500, typically 300 (at STP).

When activation is carried out at atmospheric pressure, as in the preferred embodiment, the partial pressure of hydrogen may be at least about 9 psia (400 mm Hg) preferably 12-15 psia, say 15 psia (760 mm Hg).

In the preferred second portion of the activation cycle, the hydrogen-treated catalyst may be maintained at 750° F.-1400° F., preferably 900° F.-1100° F., say 1100° F. (most preferably at about the same temperature as that employed in the first portion) in a flowing stream of hydrogen and steam. This stream may contain 15-50 mole %, preferably 20-40 mole %, say 30 mole % of hydrogen, 50-80 mole %, preferably 60-80 mole %, say 70 mole % of steam, and 0-10 mole %, preferably 0-5 mole %, say about 0 mole % of inert gas such as helium, nitrogen, or light paraffins. Preferably the gas may consist essentially of hydrogen and steam in molar ratio of 0.2-1, typically 0.25-0.6, say 0.4.

When activation is carried out at atmospheric pressure, as in the preferred embodiment, the partial pressure of hydrogen may be 100-380 mm Hg, preferably 150-300 mm Hg, say 240 mm Hg and the partial pressure of steam may be 380-660, preferably 460-610, say 520 mm Hg.

The second portion of the activation procedure may be carried out for 2-10 hours, preferably 2-5 hours, say 2 hours in a stream of flowing gas at a space velocity VHSV greater than about 1.5, preferably greater than 50, say 50-250, typically 150 (at STP).

Post activation cooling is typically carried out by maintaining the activated catalyst in a stream of flowing steam for 1-13 hours, preferably 1-5 hours, say 2 hours as the temperature is lowered to the steam dealkylation temperature of 600°-900° F., preferably 650°-900° F., say 800° F. Preferably the steam is present during post-activation in amount of 50-100 mole %, typically 80-100 mole %, say about 100 mole % of the flowing stream.

Steam dealkylation of the hydrocarbon charge may be carried out at steam dealkylating conditions by passing the charge at 600° F.-950° F., preferably 650° F.-900° F., say 800° F. and pressure of 0-400 psig, preferably 0-200 psig, say 0 psig together with steam in amount of 2-25 moles, preferably 5-15 moles, say 6 moles per mole of hydrocarbon charge (corresponding to 100%-1250%, preferably 250-750%, say 300% of the stoichiometric quantity) to a reaction zone. In commercial practice, it may be desirable to operate at e.g. 125 psig.

During steam dealkylation at these conditions, alkyl groups are removed from the charge alkylaromatic hydrocarbons to form product hydrocarbons bearing lesser numbers of alkyl groups on the aromatic nuclei. When the charge hydrocarbon contains ethylbenzenes, for example, the product stream may contain dealkylated products including benzene. When the charge hydrocarbon contains xylenes, the product stream may contain toluene, benzene, etc. When the charge hydrocarbon stream contains toluene, as in the preferred embodiment, the product hydrocarbon stream may contain benzene. In addition, the product hydrocarbon stream may contain the paraffin derived from the charge e.g. ethane or methane; and it may contain unreacted charge hydrocarbons in addition to other by-products.

Product hydrocarbon may be withdrawn from the reaction vessel and condensed. The liquid condensate may represent a recovery of 52-94 mole %, preferably 70-94 mole %, say 85 mole % of the hydrocarbon charged.

In the case of a pure toluene charge, for example, the product (per 100 moles of charge toluene) may contain, on a mole basis, the following:

TABLE

| Component | Broad | Preferred | Typical |
|---|---|---|---|
| Unreacted toluene | 4 – 79 | 13 – 70 | 37 |
| Benzene | 20 – 61 | 30 – 60 | 59 |
| Hydrogen | 20 – 183 | 90 – 180 | 165 |
| Carbon Dioxide | 20 – 61 | 30 – 60 | 55 |

In practice of the process of this invention according to one embodiment, the reaction is carried out on a short cycle basis; i.e. the reaction proper (with a charge of steam and hydrocarbon) is carried out for 0.5-2.5 minutes, preferably 0.5-2 minutes, say 1 minute and then the catalyst is regenerated by shutting off the flow of hydrocarbon for 1-7.5 minutes, preferably 1.5-6 minutes, say 3 minutes. The ratio of regeneration time to reaction time may be 1-5, preferably 2-4, say 3.

It is found during practice of the process of this invention that it is possible to achieve improved catalyst activity. For example, the toluene conversion (in terms of mole percent of toluene charge converted) may be 50%-95%, typically 85-95%, say 90% in the preferred embodiment, in contrast to comparable processes wherein the corresponding values are less than 45%.

It is also a feature of the process of this invention in its preferred embodiment, that it permits attainment of benzene yield (in terms of mole percent of the charge toluene converted to benzene) which may be 40%-60%, typically 50-55%, say 54%. Comparable processes may achieve benzene yields of less than about 35% and commonly 10%-20%.

DESCRIPTION OF PREFERRED EMBODIMENTS

Practice of the process of this invention may be apparent to those skilled in the art from the following description of preferred embodiments wherein, as elsewhere in this specification unless specifically noted, all parts and percents are parts and percents by weight. In the chemical formulae, the numbers represent molar parts as is apparent.

The catalyst support used in preparation of the catalysts of Examples I-V is a gamma alumina (derived from a Catapal S alpha alumina monohydrate) supplied by Harshaw Chemical Company in the form of 1/16 inch diameter and 0.33-0.5 in. length extrudates. This gamma alumina is substantially 100% gamma alumina. It contains no measurable sulfate anion. The principal impurity is titanium dioxide, present in amount of about 600 ppm. Other impurities include 100 ppm silica; 40 ppm $Fe_2O_3$; 50 ppm alkaline earth metal oxides (as MgO); and alkaline earth metals (as $Na_2O$) in amount too low to be detected by the usual analytical techniques — like the sulfate.

EXAMPLE I*

Solution "A" containing 527 g. of chromium nitrate nonahydrate ($Cr(NO_3)_3.9H_2O$) and 28 g. of potassium nitrate $KNO_3$ in 155 cc. of distilled water was prepared. The support (383 g.) was wetted with 390 g. (approx. 55 wt. % of the total) of solution "A" and the mixture was stirred till all the liquid was adsorbed on the support. The material was then charged to a vapor tube and heated at 700° F., to decompose the nitrates. The recovered material (448 g.) was wetted with the remainder of solution "A" and the nitrates were decomposed at 700° F., and the material was then calcined in a muffle furnace at 1000° F. for two hours. 497 g of precatalyst was recovered.

Solution "B" containing 502 g. of nickel nitrate hexahydrate ($Ni(NO_3)_2.6H_2O$) in 160 cc. distilled water was prepared. The precatalyst (497 g.) was wetted with 364 g. of Solution "B" and was stirred till all the solution was adsorbed. The nitrates were decomposed by heating at 700° F. and the decomposed material (597 g.) was wetted with the remainder of solution "B" and stirred till all the liquid was adsorbed. The nitrates were decomposed and the material was finally calcined in a muffle furnace at 700° F. for two hours. The finished catalyst (643 g.) was recovered and its analysis showed 20.0% NiO, 15.3% $Cr_2O_3$, 2.04% $K_2O$ and balance alumina.

EXAMPLE II

The support (200 g.) was treated with 1.28 g. $CaSO_4$ in 144 cc. of 5% aqueous $HNO_3$ solution. The treated alumina was dried and then calcined in a muffle furnace at 1000° F. for one hour.

The catalyst was prepared on 154 g. of $CaSO_4$ treated support using 263.3 g. of solution "A" (containing 212 g. $Cr(NO_3)_3.9H_2O$ and 11.3 g. $KNO_3$ in 40 cc. distilled water) and 238 g. of solution "B" (containing 198 g. $Ni(NO_3)_2.6H_2O$ in 40 cc. distilled water) and the procedure described in Example I above.

255 g. of finished catalyst with nominal composition 19% NiO, 15% $Cr_2O_3$, 2% $K_2O$ and 0.15% $SO_4$ (as $CaSO_4$) and 0.19% Ca on alumina was recovered.

EXAMPLE III *

200 g. of support was treated with a solution containing 1.25 g. calcium formate in 144 cc. distilled water. The treated support was dried and then calcined at 1000° F. for one hour.

The catalyst was prepared on 154 g. of calcium formate treated alumina using solutions "A" and "B" described in Example II and the procedure described in Example I.

258 g. of finished catalyst having nominal composition 19% NiO, 15% $Cr_2O_3$, 2% $K_2O$ and 0.19% Ca as calcium formate was recovered.

EXAMPLE IV 180 g. of support was treated with dilute sulfuric acid solution containing 0.86 g. conc. $H_2SO_4$ in 130 cc. distilled water. The treated alumina was dried and then calcined at 1000° F. for 2 hours. It contained 0.21% S as sulfate.

The catalyst was prepared on 160 g. of sulfuric acid treated alumina using 289.9 g. solution "A" (218 g. $Cr(NO_3)_3.9H_2O$ and 11.9 g. $KNO_3$ in 60 cc. distilled water) and 264 g. solution "B" (204 g. $Ni(NO_3)_2.6H_2O$ in 60 cc. distilled water) and the procedure described in Example I.

269 g. of finished catalyst with nominal composition 19% NiO, 15% $Cr_2O_3$, 2% $K_2O$ and 0.15% S as sulfate on alumina was recovered.

EXAMPLE V 180 g. support was treated with a solution containing 1.77 g. of $Al_2(SO_4)_3.16H_2O$ in 130 cc. of distilled water. The treated alumina was dried and then calcined in a muffle furnace at 1000° F. for one hour.

The catalyst was prepared on 160 g. of aluminum sulfate-treated alumina using the solutions "A" and "B" described in Example IV and the procedure described in Example I.

270 g. of finished catalyst having nominal composition of 19% NiO, 15% $Cr_2O_3$, 2% $K_2O$ and 0.15% S as aluminum sulfate on γ-alumina was recovered.

EVALUATION OF THE CATALYSTS

In each of the above examples, 100 cc. (or 100 g. d ≈ 1.0) of catalyst was loaded into a tubular reactor and was activated by passing $H_2$ (0.5 std. liters/min.) at 0-40 psig. and 900°-1200° F. for 14-16 hours.

In each example the catalyst was activated prior to reaction, by heating to 950° F.-1200° F. in the presence of flowing (one liter per minute) hydrogen, holding at 950° F.-1200° F. for 14-16 hours in 0.5 liters per minute of hydrogen, and then holding at 950° F.-1200° F. for 2 hours in steam (35 ml. water per hour) plus 0.5 liters per minute of hydrogen. At the end of this period, the hydrogen flow is turned off; and the reactor temperature is lowered to 800° F. and the reactor temperature is maintained in the presence of steam alone for 0.5 hours.

At this time, the flow of toluene was initiated. The average temperature in the bed of catalyst, the pressure at the input to the bed, the toluene WHSV (the weight hourly space velocity, based upon the weight of the catalyst, at which the toluene was passed through the catalytic bed), the mole ratio of steam to toluene was as noted in the Table infra.

The Table also notes the liquid hydrocarbon yield (as a weight percentage of the toluene charge) — this being the liquid which is condensed at the outlet of the catalyst bed. The analysis of the liquid hydrocarbon (based on area percent of the curve obtained by gas chromatography) is also shown.

The Table includes:

(a) the toluene conversion, as mole percent of the toluene charge;

(b) the benzene yield, as mole percent of the toluene charge; and (c) the benzene selectivity as mole percent of the toluene converted.

TABLE

| Example No. Catalyst | I* untreated | II $CaSO_4$ | III* Ca Formate | IV $H_2SO_4$ | V $Al_2(SO_4)_3$ |
|---|---|---|---|---|---|
| Run Conditions | | | | | |
| Average Bed Temp. °F | 798 | 810 | 810 | 806 | 790 |
| Pressure psig | 125 | 125 | 125 | 125 | 125 |
| Toluene WHSV, g/hr/g Cat. | 0.41 | 0.41 | 0.41 | 0.42 | 0.45 |
| Steam/Toluene - mole ratio in feed | 5.79 | 5.91 | 6.34 | 5.91 | 5.68 |
| Performance Data | | | | | |
| Liq. hydrocarbon yield wt% toluene charge | 70.86 | 87.19 | 68.55 | 87.90 | 87.60 |
| Composition of Liquid Hydrocarbon Product | | | | | |
| GC Area % | | | | | |
| Unidentified light ends | 0.04 | 0.00 | 0.00 | 0.04 | 0.04 |
| Methyl cyclopentane | 0.00 | 0.01 | 0.00 | 0.01 | 0.01 |
| cyclohexane | 0.05 | 0.27 | 0.00 | 0.01 | 0.00 |
| methylcyclohexane | 0.00 | 0.10 | 0.00 | 0.00 | 0.00 |
| benzene | 33.73 | 55.19 | 44.79 | 59.05 | 55.86 |
| toluene | 63.85 | 44.27 | 53.55 | 40.64 | 43.88 |
| C8 aromatics Toluene | 2.34 | 0.16 | 1.65 | 0.25 | 0.21 |
| Toluene Conversion, Mol %/Chg. | 53.63 | 61.31 | 63.29 | 64.31 | 61.56 |
| Benzene Yield Mol % Toluene Chg. | 28.88 | 57.20 | 36.21 | 61.16 | 57.71 |
| Benzene Selectivity, Mol % | 53.86 | 93.29 | 57.21 | 95.10 | 93.75 |

* Control Example

The data given in the Table show that under essentially identical operating conditions, the catalysts of this invention (Example IV utilizing the $H_2SO_4$-treated support, and Example V utilizing the $Al_2(SO_4)_3$-treated support) are much preferred over the control catalyst of Example I using untreated support with respect to both toluene conversion and benzene selectivity. The data obtained using the catalysts of Example II, $CaSO_4$-treated support and Example III, $Ca(HCO_2)_2$-treated support, show that sulfate ion is necessary for achieving high benzene selectivity. Furthermore, a comparison of GC data obtained in Example II, $CaSO_4$-treated support vs. Example IV, $H_2SO_4$-treated support and Example V, $Al_2(SO_4)_3$-treated support shows that the presence of calcium ions is less preferred because it promotes undesirable secondary reactions forming naphthenic materials.

Results comparable to those of Examples IV and V may be achieved when the sulfate ion is added by use of other compounds:

| Example | Source of Sulfate |
|---|---|
| VI | Nickel Sulfate |
| VII | Potassium Aluminum Sulfate |
| VIII | Potassium Bisulfate |
| IX | Methyl Sulfate |
| X | Ethyl Sulfate |
| XI | Potassium Persulfate |

Substantially improved results may also be achieved when the sulfate-modified aluminas of this invention are used as substitute for other aluminas to form catalysts by otherwise standard procedures which catalysts may be employed under standard conditions of temperature, pressure, etc. in the following reactions:

| Example | Process |
|---|---|
| XII | Hydrogenation |
| XIII | Hydrocracking |
| XIV | Transalkylation |
| XV | Disproportionation etc. |

Illustrative of other pure aluminas which may be treated by the process of this invention to yield comparable results include:

EXAMPLE XVI

Alumina prepared by reacting an aqueous solution of aluminum acetate with ammonium hydroxide, recovering the aluminum hydroxide, and dehydrating it to alumina — this alumina being substantially free of sulfate and other anions or cations;

EXAMPLE XVII

Alumina prepared by dissolving aluminum in aqueous solution of potassium hydroxide, filtering, and precipitating aluminum hydroxide by addition of acetic acid. The aluminum hydroxide on dehydrating to alumina and calcining is substantially free of anions or cations except for small amounts of potassium cation;

EXAMPLE XVIII

Alumina prepared by igniting aluminum shavings in a stream of pure oxygen.

EXAMPLE XIX

Alumina prepared by calcining the pure mineral Diaspore ($Al_2O_3.H_2O$).

EXAMPLE X

Alumina prepared by calcining the pure mineral Gibbsite (hydrargillite) — $Al_2O_3.3H_2O$.

It is a particularly outstanding feature of this invention that it is possible to activate prior art pure i.e. sulfate-free aluminas and to thereby render them capable of use as supports in catalyst systems of high activity. It has heretofore been thought that these prior art aluminas ought to be useful because of their extremely high purity; and it has not heretofore been appreciated why they were not capable of developing desired degrees of activity. It is particularly unexpected that these sulfate-free, generally pure aluminas can be activated by "sulfate-doping" — because the addition of sulfur has heretofore not been believed to produce any desirable effect; and in fact sulfur has generally been considered to be an undesirable component of catalysts. It is for this reason that prior art techniques for depositing metal on a support used not the sulfate, but rather the volatile acetate, formate, nitrate, etc. It is another unusual feature of the technique of this invention, that activation of these pure aluminas can be effected by the use of such small quantities of sulfur-containing compositions.

Although this invention has been illustrated by reference to specific embodiments, it will be apparent to those skilled in the art that various changes and modifications may be made which clearly fall within the scope of this invention.

We claim:

1. The method of preparing a treated high-purity alumina characterized by improved activity and containing a catalytic amount of sulfate anion which comprises adding to a charge high purity alumina containing less than 0.15 $SO_4^{--}$, 0.3–0.9 parts of a catalytic amount of a sulfate anion per 100 parts of $Al_2O_3$;

maintaining said charge alumina in contact with said catalytic amount of sulfate ion whereby said sulfate ion is distributed over the outside of said charge alumina and throughout substantially the entire body of said alumina thereby forming desired product treated alumina containing a catalytic amount of sulfate anion; and recovering said desired product treated alumina containing a catalytic amount of sulfate anions.

2. The method of preparing a treated high purity alumina characterized by improved activity and containing catalytic amounts of sulfate anion as claimed in claim 1 wherein said catalytic amount of sulfate anion is 0.45–0.6 parts of $SO_4^{--}$ per 100 parts of alumina.

3. The method of preparing a treated high purity alumina characterized by improved activity and containing catalytic amounts of sulfate anion as claimed in claim 1 wherein said $SO_4^{--}$ anion is introduced as $H_2SO_4$.

4. The method of preparing a treated high purity alumina characterized by improved activity and containing catalytic amounts of sulfate anion as claimed in claim 1 wherein said $SO_4^{--}$ anion is introduced as lower alkyl sulfate.

5. The method of preparing a treated high purity alumina characterized by improved activity and containing catalytic amounts of sulfate anion as claimed in claim 1 wherein said $SO_4^{--}$ anion is introduced as aluminum sulfate.

6. The method of preparing a treated high purity alumina characterized by improved activity and containing catalytic amounts of sulfate anion as claimed in claim 1 wherein said $SO_4^{--}$ anion is introduced as potassium sulfate.

7. The method of preparing a treated high purity alumina characterized by improved activity and containing catalytic amounts of sulfate anion as claimed in claim 1 wherein said $SO_4^{--}$ anion is introduced as nickel sulfate.

8. The method of preparing a treated high purity alumina characterized by improved activity and containing catalytic amounts of sulfate anion as claimed in claim 1 wherein said $SO_4^{--}$ anion is introduced as ammonium sulfate.

9. The method of preparing a treated high purity alumina characterized by improved activity and containing catalytic amounts of sulfate anion as claimed in claim 1 wherein said treated high purity alumina is a gamma alumina.

10. The method of preparing a treated high purity alumina characterized by improved activity and containing catalytic amounts of sulfate anion as claimed in claim 1 wherein said treated alumina is a catapal S alumina.

11. The method of preparing a treated high-purity alumina characterized by improved activity from a charge high-purity alumina containing less than about 0.15% sulfate anion as claimed in claim 1 wherein said sulfate anion is added in the form of a sulfate precursor.

12. The method of preparing a treated high-purity alumina characterized by improved activity from a charge high-purity alumina containing less than about 0.15% sulfate anion as claimed in claim 1 wherein said sulfate anion is added as sulfuric acid, aluminum sulfate, ammonium sulfate, calcium sulfate, or methyl sulfate.

13. The method of preparing a treated high purity gamma alumina characterized by improved activity and containing a catalytic amount of sulfate anion which comprises contacting said charge high purity gamma alumina containing less than about 0.15% sulfate with sulfuric acid whereby a catalytic amount of sulfate anion together with hydrogen, is adsorbed therein, maintaining said charge high purity gamma alumina in contact with said sulfuric acid whereby a catalytic amount of sulfate ion is distributed over the outside of said charge alumina and throughout substantially the entire body of said alumina thereby forming desired product treated gamma alumina containing catalytic amounts of sulfate anions together with hydrogen; and recovering said desired product treated gamma alumina containing catalytic amounts of sulfate anions together with hydrogen.

14. The method of preparing a treated high purity alumina containing catalytic amounts of sulfate anion which comprises adding to a charge high purity alumina selected from the group consisting of alpha alumina trihydrate, beta alumina trihydrate, alpha alumina monohydrate, and gamma alumina, a catalytic amount of a sulfate ion;

maintaining said charge alumina in contact with said catalytic amount of sulfate ion whereby said sulfate ion is distributed over the outside of said charge alumina and throughout substantially the entire body of said alumina thereby forming desired product treated alumina containing a catalytic amount of sulfate anions; and recovering said desired product treated alumina containing a catalytic amount of sulfate anions.

15. An alumina composition characterized by improved activity consisting essentially of (1) alumina containing less than about 0.15% sulfate and added thereto (2) a catalytic amount of sulfate anion, wherein said catalytic amount of sulfate anion is 0.3–0.9 parts of $SO_4^{--}$ per 100 parts of alumina.

16. An alumina as claimed in claim 15, characterized by improved activity, containing catalytic amount of sulfate ion distributed over the outside of said alumina and throughout substantially the entire body of said alumina.

17. An alumina as claimed in claim 15, wherein said catalytic amount of sulfate anion is 0.45w%–0.6w% of said alumina.

18. An alumina as claimed in claim 15, wherein said sulfate anion is introduced as aluminum sulfate.

19. An alumina as claimed in claim 15, wherein said $SO_4^{--}$ anion is introduced as $H_2SO_4$.

20. An alumina characterized by improved activity and containing a catalytic amount of sulfate anion, containing less than about 0.15% $SO_4^{--}$, prepared by the process which comprises adding to a charge high purity alumina a catalytic amount of a sulfate anion;

maintaining said charge alumina in contact with said catalytic amount of sulfate ion whereby said sulfate ion is distributed over the outside of said charge alumina thereby forming desired product treated alumina containing a catalytic amount of sulfate anions; and recovering said desired product treated alumina containing a catalytic amount of sulfate anions.

21. The method of preparing a treated high-purity alumina characterized by improved activity from a charge high-purity alumina containing less than about 0.15% sulfate anion as claimed in claim 11 wherein said sulfate precursor is bisulfate.

22. The method of preparing a treated high-purity alumina characterized by improved activity from a charge high-purity alumina containing less than about 0.15% sulfate anion as claimed in claim 11 wherein said sulfate precursor is sulfonate.

23. The method of preparing a treated high-purity alumina characterized by improved activity from a charge high-purity alumina containing less than about 0.15% sulfate anion as claimed in claim 11 wherein said sulfate precursor is sulfite.

24. The method of preparing a treated high-purity alumina characterized by improved activity from a charge high-purity alumina containing less than about 0.15% sulfate anion as claimed in claim 11 wherein said sulfate precursor is bisulfite.

25. The method of preparing a treated high-purity alumina characterized by improved activity from a charge high-purity alumina containing less than about 0.15% sulfate anion as claimed in claim 11 wherein said sulfate precursor is thiosulfate.

26. The method of preparing a treated high-purity alumina characterized by improved activity from a charge high-purity alumina containing less than about 0.15% sulfate anion as claimed in claim 11 wherein said sulfate precursor is persulfate.

* * * * *

UNITED STATES PATENT AND TRADEMARK OFFICE
CERTIFICATE OF CORRECTION

PATENT NO. : 4,139,491

DATED : February 13, 1979

INVENTOR(S) : T. G. Dorawala et al

It is certified that error appears in the above-identified patent and that said Letters Patent are hereby corrected as shown below:

Please correct claim 20 to read as follows:

20. An alumina characterized by improved activity and containing a catalytic amount of sulfate anion prepared by the process which comprises:

adding to a charge high purity alumina containing less than about 0.15% sulfate a catalytic amount of a sulfate anion;

maintaining said charge alumina in contact with said catalytic amount of sulfate ion whereby said sulfate ion is distributed over the outside of said charge alumina thereby forming desired product treated alumina containing a catalytic amount of sulfate anions; and recoverying said desired product treated alumina containing a catalytic amount of sulfate anions.

Signed and Sealed this

*Eleventh* Day of *December 1979*

[SEAL]

*Attest:*

SIDNEY A. DIAMOND

*Attesting Officer*     *Commissioner of Patents and Trademarks*